US011117880B2

(12) United States Patent
Weaver et al.

(10) Patent No.: US 11,117,880 B2
(45) Date of Patent: Sep. 14, 2021

(54) FACILE AND SELECTIVE PERFLUORO- AND POLYFLUOROARYLATION OF MELDRUM'S ACID

(71) Applicant: The Board of Regents for Oklahoma State University, Stillwater, OK (US)

(72) Inventors: Jimmie Dean Weaver, Stillwater, OK (US); Sameera Senaweera, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 0 days.

(21) Appl. No.: 16/404,110

(22) Filed: May 6, 2019

(65) Prior Publication Data

US 2019/0256488 A1    Aug. 22, 2019

Related U.S. Application Data

(63) Continuation of application No. 14/840,951, filed on Aug. 31, 2015, now Pat. No. 10,316,014.

(60) Provisional application No. 62/043,650, filed on Aug. 29, 2014.

(51) Int. Cl.
| | |
|---|---|
| *C07D 319/06* | (2006.01) |
| *C07D 319/08* | (2006.01) |
| *C07D 405/04* | (2006.01) |
| *C07D 405/10* | (2006.01) |
| *C07D 413/10* | (2006.01) |

(52) U.S. Cl.
CPC ......... *C07D 319/08* (2013.01); *C07D 319/06* (2013.01); *C07D 405/04* (2013.01); *C07D 405/10* (2013.01); *C07D 413/10* (2013.01)

(58) Field of Classification Search
CPC .................................................. C07D 319/06
See application file for complete search history.

(56) References Cited

U.S. PATENT DOCUMENTS 10,316,014 B2 * 6/2019 Weaver ................ C07D 405/10

OTHER PUBLICATIONS

American Chemical Society Chemical Abstract Service. CAS RN #: 142603-30-3. Public availability date/Date entered into STN: Jul. 24, 1992. (Year: 1992).*
International Union of Pure and Applied Chemistry. "Arenes." First available to the public: Feb. 24, 2014. Accessed Jan. 18, 2020. Available at: < http://goldbook.iupac.org/terms/view/A00435 > . (Year: 2014).*
Lecointre, B., et al. "Mild addition of carbon nucleophiles to pyridine and quinoline N-oxides under different activation conditions." Tetrahedron Letters. (2014), vol. 55, pp. 1913-1915. (Year: 2014).*
Kidwai, M., et al. "Laccase-catalysed reaction between Meldrum's acid and catechols/hydroquinones—An investigation." C.R. Chimie. (2013), vol. 16, pp. 728-735. (Year: 2013).*
Arnett, et al.; "Ion Pairing and Reactivity of Enolate Anions. 5, Thermodynamics of Ionization of β-Di- and Tricarbonyl Compounds in Dimethyl Sulfoxide Solution and Ion Pairing of Their Alkali Salts," J. Am. Chem. Soc. (1984), vol. 106, pp. 6759-6767.
Chen, et al.; "Polyvalent Iodine in Synthesis I. An Efficient Route to Isopropylidene Arylmalonates (5-Aryl-Substituted Meldrum's Acid)," J. Org. Chem. (1987), vol. 52, pp. 4115-4117.
Chidipudi, et al.; "Functionalization of Csp3—H and Csp2—H Bonds: Synthesis of Spiroindenes by Enolate-Directed Ruthenium-Catalyzed Oxidative Annulation of Alkynes with 2-Aryl-1,3-Dicarbobnyl Compounds," Angew. Chem. Int. Ed. (2012), vol. 51, pp. 12115-12119.
Craig, et al.; "Decarboxylative Claisen Rearrangement Reactions of Allylic Tosylmalonate Esters," American Chemical Society (2005), vol. 7, No. 3, pp. 463-465.
Davidson, et al.; "The Structure of Meldrum's Supposed β-Lactonic Acid," J. Chem. Soc. (1948), vol. 70, pp. 3426-3428.
Dumas, et al.; "Meldrum's Acids and 5-Alkylidene Meldrum's Acids in Catalytic Carbon-Carbon Bond Forming Processes," Accounts of Chemical Research (2010), vol. 43, No. 3, pp. 440-454.
Fillion, et al.; "Synthesis of Fused 4,5-Disubstituted Indole Ring Systems by Intramolecular Friedel-Crafts Acylation of 4-Substituted Indoles," J. Org. Chem. (2008), vol. 73, No. 7, pp. 2920-2923.
Ghosh, et al.; "Intramoledular Dehydrogenative Coupling of sp2 C—H and sp3 C—H Bonds: An Expeditious Route to 2-Oxindoles," American Chemical Society (2012), vol. 14, No. 23, pp. 5864-5867.
Hansen, et al.; "Highly Efficient Asymmetric Synthesis of Sitagliptin," J. Am. Chem. Soc. (2009), vol. 131, No. 25, pp. 8798-8804.
Kimmel, et al.; "Enantio- and Diastereoselective Addition of Cyclohexyl Meldrum's Acid to 3- and a3-Disubstituted Nitroalkenes Via N-Sulfinyl Urea Catalysis," Chem. Sci. (2012), vol. 3, pp. 121-125.
Lecointre, et al.; "Mild Addition of Carbon Nucleophiles to Pyridine and Quinoline N-Oxides Under Different Activation Conditions," Tetrahedron Letters (2014) No. 55, pp. 1913-1915.
Lipson, et al.; "One Hundred Years of Meldrum's Acid: Advances in the Synthesis of Pyridine and Pyrimidine Derivatives," Mol Divers (2009), vol. 13, pp. 399-419.
Liu, et al.; "Catalytic Asymmetric Intermolecular Stetter Reaction of Glyoxamides with Alkylidenemalonates," J. Am. Chem. Soc. (2008), vol. 130, pp. 14066-14067.

(Continued)

*Primary Examiner* — John S Kenyon
(74) *Attorney, Agent, or Firm* — Dunlap Codding, P.C.

(57) ABSTRACT

This disclosure relates generally to the facile and selective mono-perfluoro and poly-fluoroarylation of Meldrum's acid to generate a versatile synthon for highly fluorinated alpha-phenyl acetic acid derivatives which provide straightforward access to fluorinated building blocks. The reaction takes place quickly and all products were isolated without the need for chromatography. An embodiment provides an alternative strategy to access alpha-arylated Meldrum's acids which avoids the need for aryl-Pb(IV) salts or diaryliodonium salts and provides access to the tertiary product which was not previously synthetically accessible. The synthetic versatility and utility of the Meldrum's acid products is demonstrated by subjecting the products to several derivatizations of the Meldrum's acid products as well as photocatalytic hydrodefluorination which provide access to difficult but valuable synthetic targets such as multifluorinated aromatics.

20 Claims, 8 Drawing Sheets

(56) References Cited

OTHER PUBLICATIONS

Lucius, et al.; "Kinetic Studies of Carbocation-Carbanion Combination: Key to a General Concept of Polar Organic Reactivity," Angew. Chem. Int. (2002), vol. 41, No. 1, pp. 91-95.
Meldrum, Andrew N.; "A β-Lactonic Acid from Acetone and Malonic Acid," Journal of the Chemical Society (1908), vol. 93, pp. 598-601.
Olmstead, et al.; "Ion-Pair Association Constants in Dimethyl Sulfoxide," J. Org. Chem. (1980), vol. 45, No. 16, pp. 3299-3305.
Saidi, et al.; "A One Pot Synthesis of 5-Phenyl-1, 3-Dioxane-4, 6-Dione Derivatives, Synthetic Communications: An International Journal for Rapid Communication of Synthetic Organic Chemistry," Synthetic Communications (2000), vol. 30, No. 13, pp. 2345-2351.
Sato, et al.; "An Efficient Method for Generation of α-Oxoketenes: Cycloreversion of Enolized Meldrum's Acid Derivatives," Tetrahedron Letters (1997), vol. 38, No. 38, pp. 6689-6692.
Senaweera, et al.; "Photocatalytic Hydrodefluorination: Facile Access to Partially Fluorinated Aromatics," J. Am. Chem. Soc. (2014), vol. 136, pp. 3002-3005.
Sigma-Aldrich; "2,2-dimethyl-1,3-dioxane-4,6-dione," 2017. Available from: <http://www.sigmaaldrich.com/catalog/product/aldrich/210145?lang=en&region=US#>.
Mohammed, et al.; "Studies on Tertiary Amine Oxides. LXXV. Reactions of Aromatic N-oxides with Meldrum's Acid in the Presence of Acetic Anhydride," Chem. Pharm. Bull. (1982), vol. 30, No. 5, pp. 1680-1691.
Bamzadeh, et al.; "Electrochemical Oxidation of Catechols in the Presence of Phenyl-Meldrum's Acid. Synthesis and Kinetic Evaluation," Chem. Pharm. Bull. (2010) vol. 58, No. 1, pp. 23-26.

\* cited by examiner

*Chen and Stang*

} Prior Art

*Pinhey*

Figure 1C *This work*

| Entry | Deviation from standard conditions | Time (min) | % Conv.[a] |
|---|---|---|---|
| 1 | None | 120/300 | 93/100 |
| 2 | DMSO | 120/300 | 100/100 |
| 3 | DMA | 120/300 | 100/100 |
| 4 | IPA | 120/300 | 3/6 |
| 5 | DCM | 120/300 | 17/28 |
| 6 | Tol | 120/300 | ND[b] |
| 7 | THF | 120/300 | 13/23 |
| 8 | TEA instead of DIPEA | 120/300 | 87/100 |
| 9 | $K_2CO_3$ instead of DIPEA | 120/300 | 10/15 |
| 10 | 0.05 M in MeCN | 270 | 45 |
| 11 | 0.1 M in MeCN | 270 | 73 |
| 12 | 0.2 M in MeCN | 270 | 100 |
| 13 | 1.0 M in MeCN | 20 | 100 |

[a]Conversions determined by $^{19}$F NMR. [b]ND = not detected.

Figure 3

Yields correspond to isolated DIPEA-ammonium salts

Figure 4

Yields correspond to isolated DIPEA-ammonium salts

FACILE AND SELECTIVE PERFLUORO- AND POLYFLUOROARYLATION OF MELDRUM'S ACID

CROSS REFERENCE TO RELATED APPLICATIONS

This application is a continuation of U.S. Ser. No. 14/840,951, filed Aug. 31, 2015; which claims benefit under 35 USC § 119(e) of U.S. Provisional Application Ser. No. 62/043,650, filed Aug. 29, 2014. The entire contents of each of the above-referenced patent applications are hereby expressly incorporated herein by reference.

TECHNICAL FIELD

This application relates generally to chemical methods and, more generally, to systems and methods for direct arylations of Meldrum's acid.

BACKGROUND

Meldrum's acid was initially discovered in 1908 by Meldrum. However, the structure was not correctly identified for the next 40 years until it was correctly assigned by Davidson. Due to its anomalous acidity (pKa=7.3 in DMSO) Meldrum's acid has a long and rich history as an activated nucleophile and, contrary to its malonate cousin, it can be hydrolyzed easily under acidic conditions which can allow for facile elaboration not possible with malonates.

While strategies for the selective alkylation of Meldrum's acid have been well developed, such as the reductive alkylation of aldehydes, coupling and reduction of carboxylic acids, their addition to Michael acceptors, substitution of Mitsunubu reagents, and alkyl halides, addition to cationic metal allyls- the corresponding arylation is far less developed.

Figure 1A:
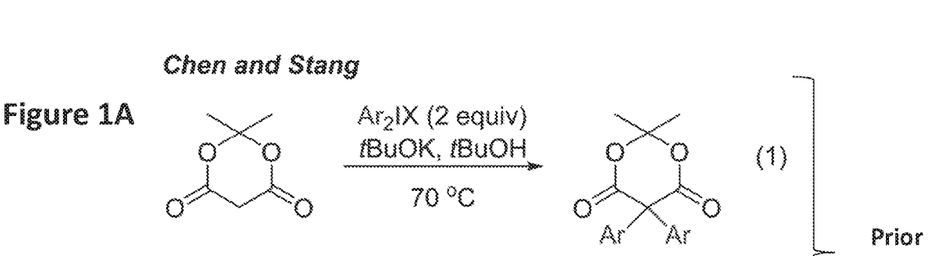
FIGS. 1A, 1B, and 1C contain schematic illustrations of prior art approaches (A) and (B) and an embodiment of the approach taught herein (C).
Figure 1B:
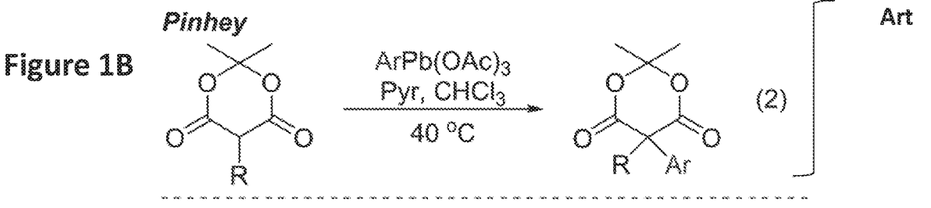

In contrast to alkylation of Meldrum's acid, very few methods exist for the direct alpha-arylation of Meldrum's acid. In fact, most commonly this motif is achieved via acetal or ketal formation of a malonic acid or its ketene derivative. A more direct approach would be to alpha-arylate an already existing Meldrum's acid unit. Towards this goal, Chen and Stang have shown that diaryliodonium salts can afford direct arylation of Meldrum's acid (FIG. 1A). Furthermore, Pinhey has shown that aryl-leadtriacetates undergo facile coupling with Meldrum's acid (FIG. 1B). Unfortunately, neither of these methods allows for selective monoarylation as the reaction always leads to the fully quaternerized adduct.

Thus, what is needed are methods that allow for the selective monoarylation of Meldrum's acid that possess a tertiary center or unsymmetric quaternerized center.

Before proceeding to a description of the inventive concept(s), however, it should be noted and remembered that the description of the present disclosure which follows, together with the accompanying drawings, should not be construed as limiting the inventive concept(s) to the examples (or embodiments) shown and described. This is so because those skilled in the art to which the present disclosure pertains will be able to devise other forms of the inventive concept(s) within the ambit of the appended claims.

BRIEF DESCRIPTION OF THE DRAWINGS

These and further aspects of the present disclosure are described in detail in the following examples and accompanying drawings.

DETAILED DESCRIPTION

While the present disclosure is susceptible of embodiment in many different forms, there is shown in the drawings, and will herein be described hereinafter in detail, some specific embodiments of the present disclosure. It should be understood, however, that the present disclosure is to be considered an exemplification of the principles of the inventive concept(s) and is not intended to limit the inventive concept(s) to the specific embodiments or algorithms so described.

It is to be understood that the terms "including," "comprising," "consisting," and grammatical variants thereof do not preclude the addition of one or more components, features, steps, or integers or groups thereof and that the terms are to be construed as specifying components, features, steps, or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may," "might," "can," or "could" be included, that particular component, feature, structure, or characteristic is not required to be included.

Where applicable, although state diagrams, flow diagrams or both may be used to describe embodiments, the present disclosure is not limited to those diagrams or to the corresponding descriptions. For example, flow need not move through each illustrated box or state, or in exactly the same order as illustrated and described.

Methods of the present disclosure may be implemented by performing or completing manually, automatically, or a combination thereof, selected steps or tasks.

The term "method" may refer to manners, means, techniques, and procedures for accomplishing a given task including, but not limited to, those manners, means, techniques and procedures either known to, or readily developed from known manners, means, techniques, and procedures by practitioners of the art to which the present disclosure belongs.

For purposes of the instant disclosure, the term "at least" followed by a number is used herein to denote the start of a range beginning with that number (which may be a ranger having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Terms of approximation (e.g., "about," "substantially," "approximately," etc.) should be interpreted according to their ordinary and customary meanings as used in the associated art unless indicated otherwise. Absent a specific definition and absent ordinary and customary usage in the associated art, such terms should be interpreted to be ±10% of the base value.

When, in this document, a range is given as "(a first number) to (a second number)" or "(a first number)-(a second number)," this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Further, it should be noted that terms of approximation (e.g., "about," "substantially," "approximately," etc.) are to be interpreted according to their ordinary and customary meanings as used in the associated art unless indicated otherwise herein. Absent a specific definition within this disclosure, and absent ordinary and customary usage in the associated art, such terms should be interpreted to be plus or minus 10% of the base value.

According to an embodiment, there is provided a facile and selective monoperfluoroarylation and polyfluoroarylation of Meldrum's acid to generate a versatile synthon for highly fluorinated alpha-phenyl acetic acid derivatives which provide straightforward access to fluorinated building blocks. The reaction takes place quickly and most products were isolated without the need for chromatography. Importantly, this method provides an alternative strategy to access alpha-arylated Meldrum's acids which avoids the need for aryl-Pb(IV) salts or diaryliodonium salts. Furthermore, the synthetic versatility and utility of the Meldrum's acid products is demonstrated by subjecting the products to several derivatizations of the Meldrum's acid products as well as photocatalytic hydrodefluorination.

Conditions that allow for clean, rapid, and operationally simple monoarylation of Meldrum's acid and its derivatives with a number of highly fluorinated arenes are taught herein. Furthermore, these adducts are demonstrated to be easily functionalizable and undergo typical reactions expected of Meldrum's acid.

The Meldrum's acid (MA) of the present disclosure may be unsubstituted, or it may be a Meldrum's acid analog variant. For the purpose of the present disclosure, the term Meldrum's acid shall include the unsubstituted form and all analog variants.

The foregoing has outlined in broad terms some of the more important features of the present disclosure disclosed herein so that the detailed description that follows may be more clearly understood, and so that the contribution of the instant inventors to the art may be better appreciated. The present disclosure is not to be limited in its application to the details of the construction and to the arrangements of the components set forth in the following description or illustrated in the drawings. Rather, the present disclosure is capable of other embodiments and of being practiced and carried out in various other ways not specifically enumerated herein. Finally, it should be understood that the phraseology and terminology employed herein are for the purpose of description and should not be regarded as limiting, unless the specification specifically so limits the inventive concept(s).

Figure 1C:
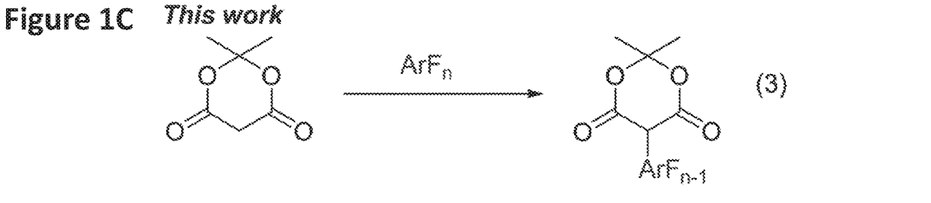

According to an embodiment, the instant disclosure teaches increasing the number of fluorinated arene building blocks as well as methods for their further elaboration. A method for direct per(poly)fluoroarylation of Meldrum's acid would be particularly ideal given the versatility of Meldrum's acid. Given that perfluoroarenes are known to readily undergo nucleophilic aromatic substitution ($S_NAr$), it was surprising to find that the addition of Meldrum's acid had never been reported (equation (3), FIG. 1), and an effort was initiated to develop this reaction. One goal was to determine whether Meldrum's acid is a competent nucleophile for $S_NAr$ reactions of highly fluorinated arenes.

Figure 2:
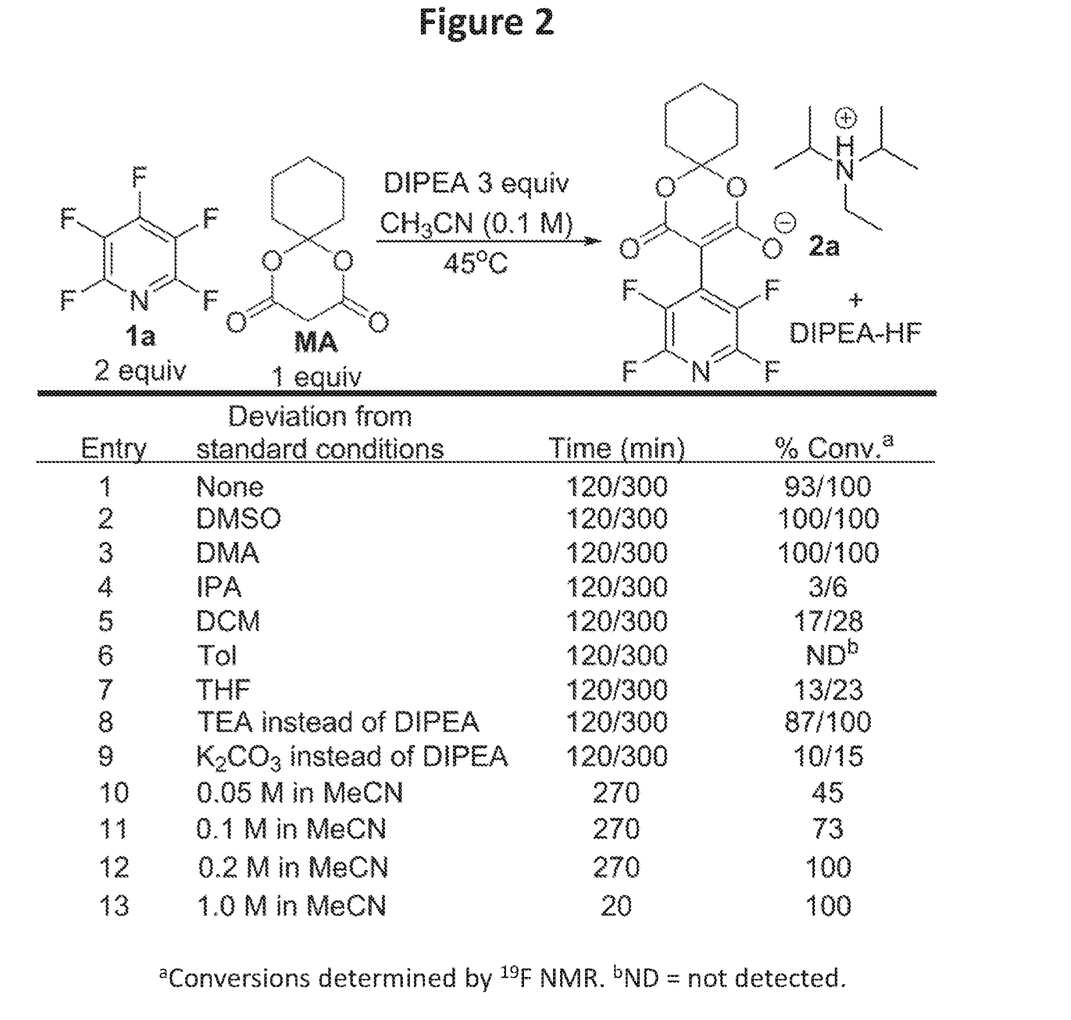
FIG. 2 illustrates an example data set that teaches an approach to optimization of reaction conditions.
Figure 10:
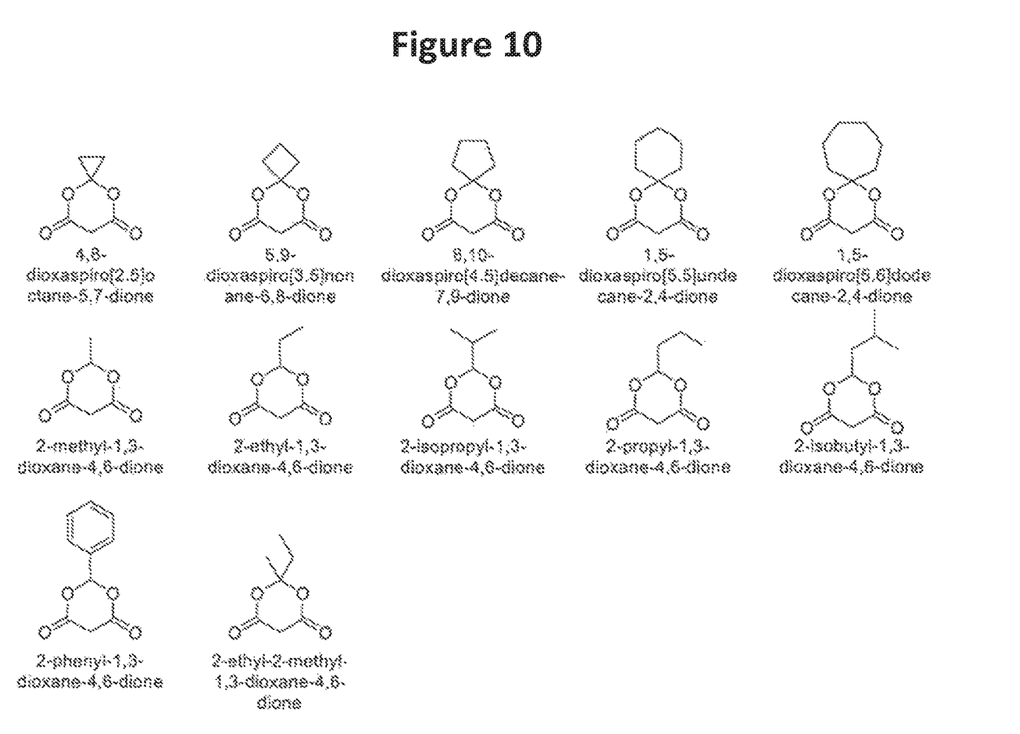
FIG. 10 contains an exemplary Meldrum's acid analog with variations at the O,O-carbon of the present disclosure.

One particularly suitable approach to the reaction of the present disclosure uses pentafluoropyridine and 1,5-dioxaspiro[5.5]undecane-2,4-dione (MA) in which the normal [2,2]dimethyl group has been replaced with a cyclohexyl group—which is more soluble in most organic solvents and displays a greater hydrolytic stability than simple Meldrum's acid (2,2-dimethyl-1,3-dioxane-4,6-diene) which can be prone to hydrolysis over prolonged time periods, along with diisopropylethylamine (DIPEA) in acetonitrile (FIG. 2). It should be understood, however, that unsubstituted MA is suitable (if not optimal) for the reaction of the present disclosure as well as other Meldrum's acid variants which are also contemplated. By way of example, and not limitation, suitable Meldrum's acid analog may be varied at the α position (described further below) or may be varied at the O,O-carbon. Exemplary known suitable Meldrum's acid analog varied at the O,O-carbon are set out in FIG. 10 and may bear a single alkyl group (row 2), an aryl group (row 3), two alkyl groups (row 3), or cyclic alkyl groups (row 1). It will be understood by one of skill in the art that others may also be suitable and are contemplated.

The reaction of a particular (but non-limiting) embodiment can include the addition of a base. A suitable base for the present disclosure is one which is sufficiently basic to deprotonate Meldrum's acid. In addition, such a base is not prone to nucleophilic substitution.

In looking at the data in the table of FIG. 2, several trends became clear. First, polar aprotic solvents worked well (entries 1-3) while protic-(entry 4), halogenated-(entry 5), aromatic-(entry 6), and ethereal-solvents (entry 7) were found to be inferior. Polar-aprotic solvents as well as ionic liquids would both likely serve as good solvent mediums for the reaction of the present disclosure. As is evident above and in FIG. 2, the solvents that did work well are examples of polar-aprotic solvents. It will be understood by one of skill in the art that industry has more of these types of solvents on hand, and it is contemplated that another could work better. Ionic liquids, commonly characterized as salt compounds which are liquid below 100° C., also facilitate reactions that go through charged intermediates (as is the case in the reaction of the present disclosure). However, one skilled in the art would recognize that there are some subtleties about whether this is actually a solvent. It is a salt and therefore has no vapor pressure and so is by some definition arguably not a solvent at all. However, it does serve as the reaction medium as does the solvent, hence the word choice. It should be understood that the term "solvent" as used herein for the purpose of the present disclosure would also include ionic liquids.

Acetonitrile was the solvent medium used for further studies because its comparatively greater volatility facilitated isolation. Additionally, both triethylamine (entry 8) and K$_2$CO$_3$ (entry 9) were screened as bases. While triethylamine gave similar conversions to the standard reaction (entry 1), it also yielded an undesirable N-arylated side-product. Thus, DIPEA was used for further studies. Finally, the effect of concentration was examined (entries 10-13). The rate of the reaction displayed a dependency on the concentration, and thus the reactions were run at 1 M in order to shorten the reaction times.

In an alternate embodiment, the reaction of the present disclosure could take place neat, i.e., without solvent. It is contemplated that the reaction would work as well or possibly better without any additional solvent. The amine and the acid would most likely form a salt melt which could go on to react with the perfluoroarene to give product. From a production standpoint, this would be attractive since it would reduce the amount of solvent used and the waste generated.

With conditions in hand that provided product with remarkable speed and essentially free of unwanted side products, a workup of conditions that would allow isolation of the DIPEA-adduct salt from left over perfluoroarene were investigated, i.e., in this embodiment DIPEA and DIPEA-HF salt. This was accomplished through a series of evaporation, solvent change, and washing which resulted in analytically pure product. The workups allowed rapid isolation in high yield with no need for column chromatography which should facilitate its implementation on a larger scale.

Figure 3:
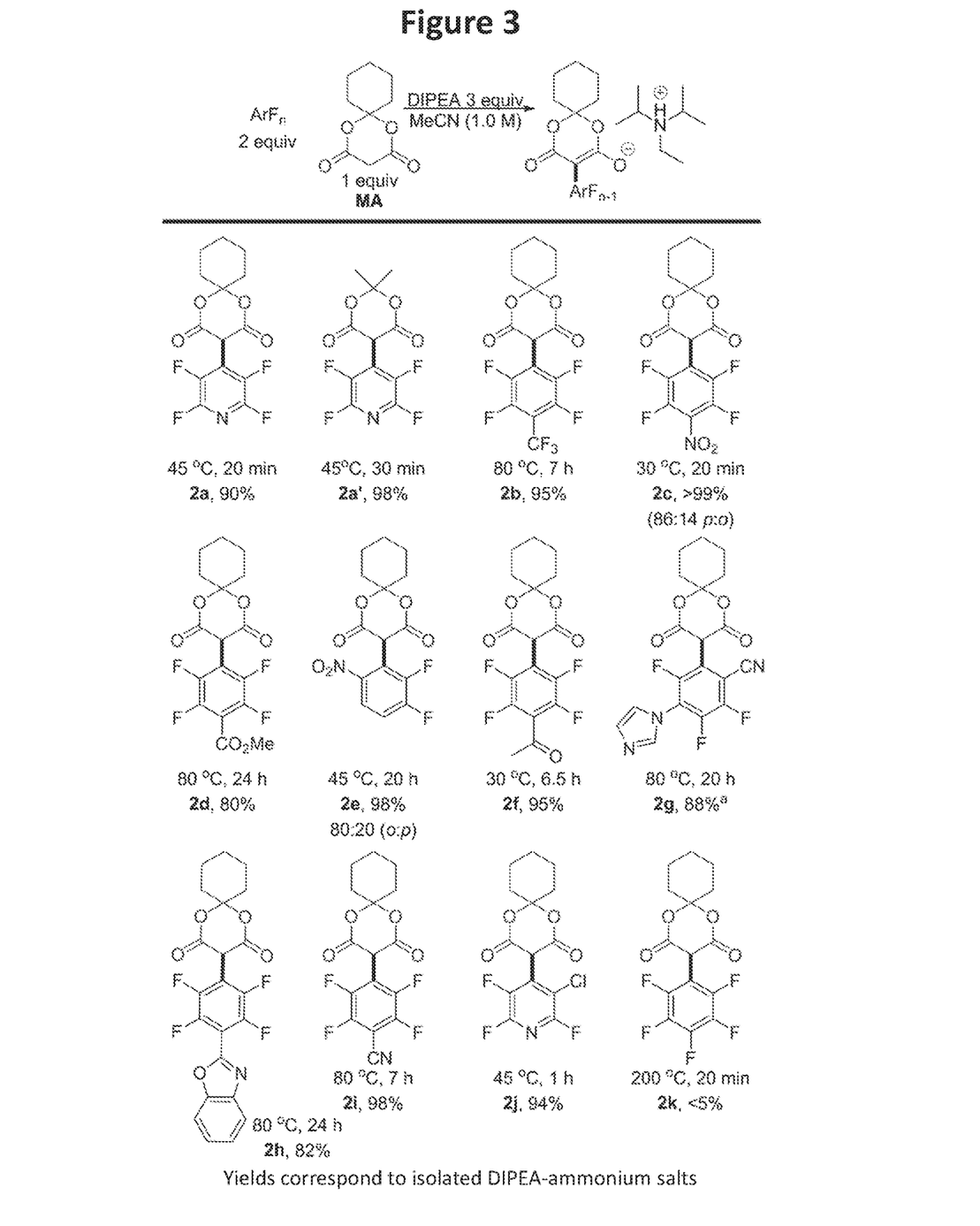
FIG. 3 illustrates the addition of unsubstituted MA to fluorinated arenes.

Given the reaction and workup conditions, the scope of the reaction was evaluated. In general, this reaction works extremely well for fluoroarenes that possess an activating functional group (i.e. an electron withdrawing group) (FIG. 3). Specifically, the reaction worked well for pyridines (2a, 2a', and 2j), nitro-substituted substrates (2c and 2e), ketones (2f), nitriles (2g and 2i), and esters (2d), as well as trifluoromethyl groups (2b) and heterocycle substituted groups (2g and 2h). One of skill in the art would recognize that difluoromethyl groups would work as well. Selective addition to the C-4 (fluorine bearing) of 3-chloro-2,4,5-trifluoropyridine is consistent with the S$_N$Ar mechanism. The absolute control of monoarylation vs. diarylation is remarkable considering that the previous methods were unable to selectively monoarylate.

Figure 4:
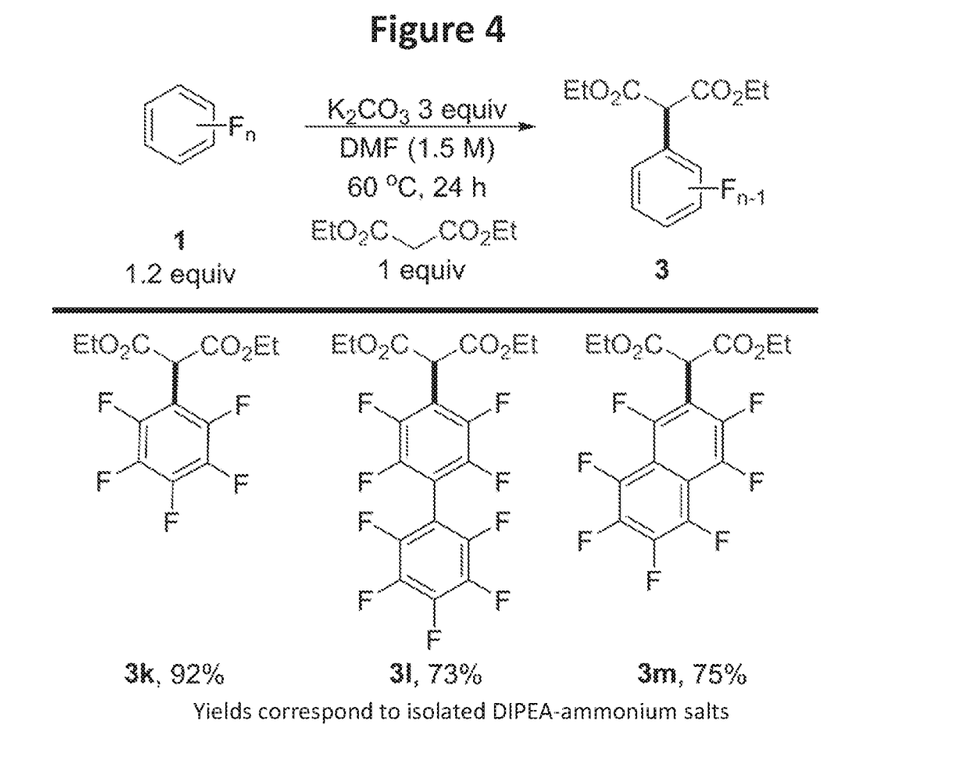
FIG. 4 illustrates the addition of diethylmalonate to unactivated perfluoroarenes.

Empirical results indicate a less productive result for simple hexafluorobenzene even at elevated temperatures (200° C.) where it remained mostly unchanged. It did, however, demonstrate the robustness of MA at high temperatures under basic conditions—as no decomposition products could be detected. Speculating that the lack of reactivity of hexafluorobenzene is attributed to an insurmountable reaction barrier, it was reasoned that this might be overcome by increasing the reactivity of the nucleophile. To accomplish this, malonate ester was used, which is significantly more basic (diethyl malonate pKa=16.4 in DMSO) and correspondingly more nucleophilic. The use of the malonate did indeed lead to clean substitution of even the least activated of the perfluoroarenes (FIG. 4). While it would have been preferred to have used Meldrum's acid as the nucleophile due to its synthetic versatility, ultimately the 1,3-diester motif was still obtained using diethyl malonate for hexafluorobenzene (3k), decafluorobiphenyl (3l), and perfluoronaphthalene (3m), FIG. 4.

Figure 5:
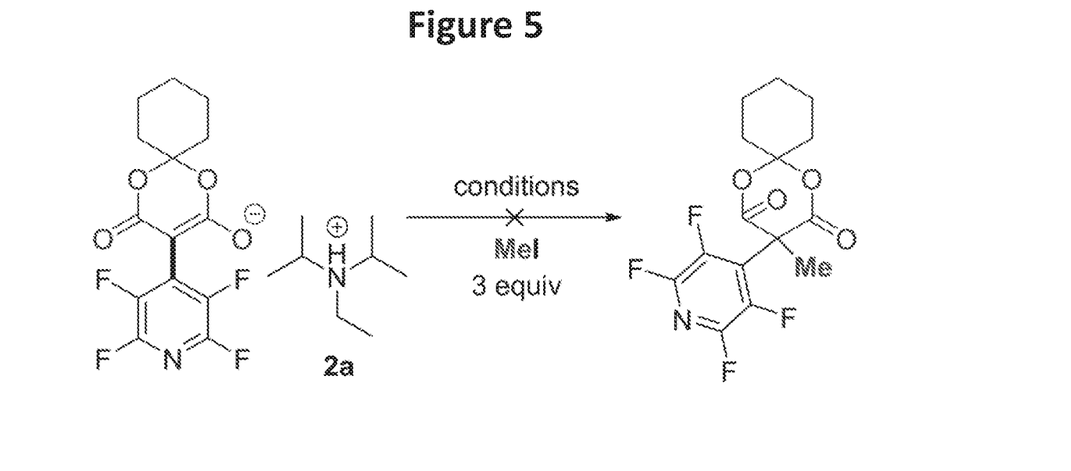
FIG. 5 illustrates a failed direct alkylation of the adducts.

Next, an effort was made to fully quaternerize the remaining activated methine via alkylation (FIG. 5). However, after several failed attempts to methylate 2a via standard alkylation techniques, this strategy was reevaluated. The lack of alkylation could have been due to either steric or electronic inhibition (or alternatively a combination of both). It was suspected that the additional stabilization of the MA-carbanion by the perfluoroarene significantly reduced the nucleophilicity of the carbanion, and that the rate of alkylation and subsequent arylation) was slow due more to the electronics than the steric inhibition of the transition state. Steric inhibition seems less likely given that there are numerous examples of quaternerized Meldrum's acid compounds that were achieved via alkylation, though admittedly there are no examples of alkylations of α-(2,6-disubstituted aryl)-Meldrum's acid. Nonetheless, the planned route to the fully quaternerized carbons was reconsidered.

Figure 6:
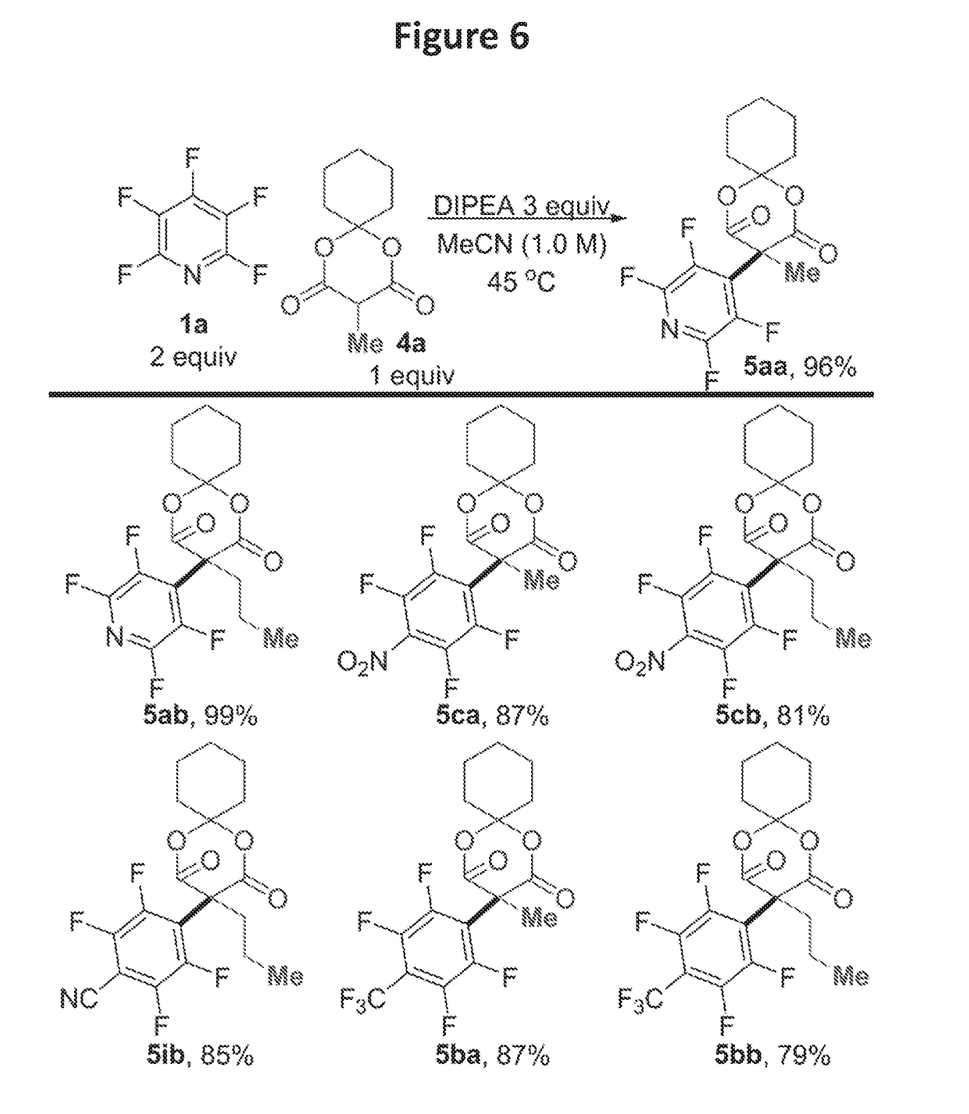
FIG. 6 illustrates the addition of α-alkylated MA's to perfluoroarenes.

Next, the order of events was reversed. Using αalkylated Meldrum's acid derivatives made it possible to facilitate the S$_N$Ar reaction to arrive at the desired fully substituted Meldrum's acid derivatives (FIG. 6). The additions took place smoothly with no alterations from the initial conditions despite the fact that the reaction forms a quaternary center, hinting that the inability to alkylate 2a is an electronic rather than a steric issue. As can be seen from FIG. 6, the yields are good to excellent and to the first approximation take place with similar rates to the corresponding perfluoroarylation (i.e., FIG. 3).

As would be apparent to one of ordinary skill in the art, α-aryl, α-alkoxy, and α-thio Meldrum's acid derivatives would work as well and could be substituted for the α-alkylated Meldrum's acid. Additionally, and by way of example and not limitation, the Meldrum's acid of these alternate embodiments could be a compound of the form:

where X represents OH, OAc, NHAc, SMe, CL, Br, or Ph.

Figure 7:
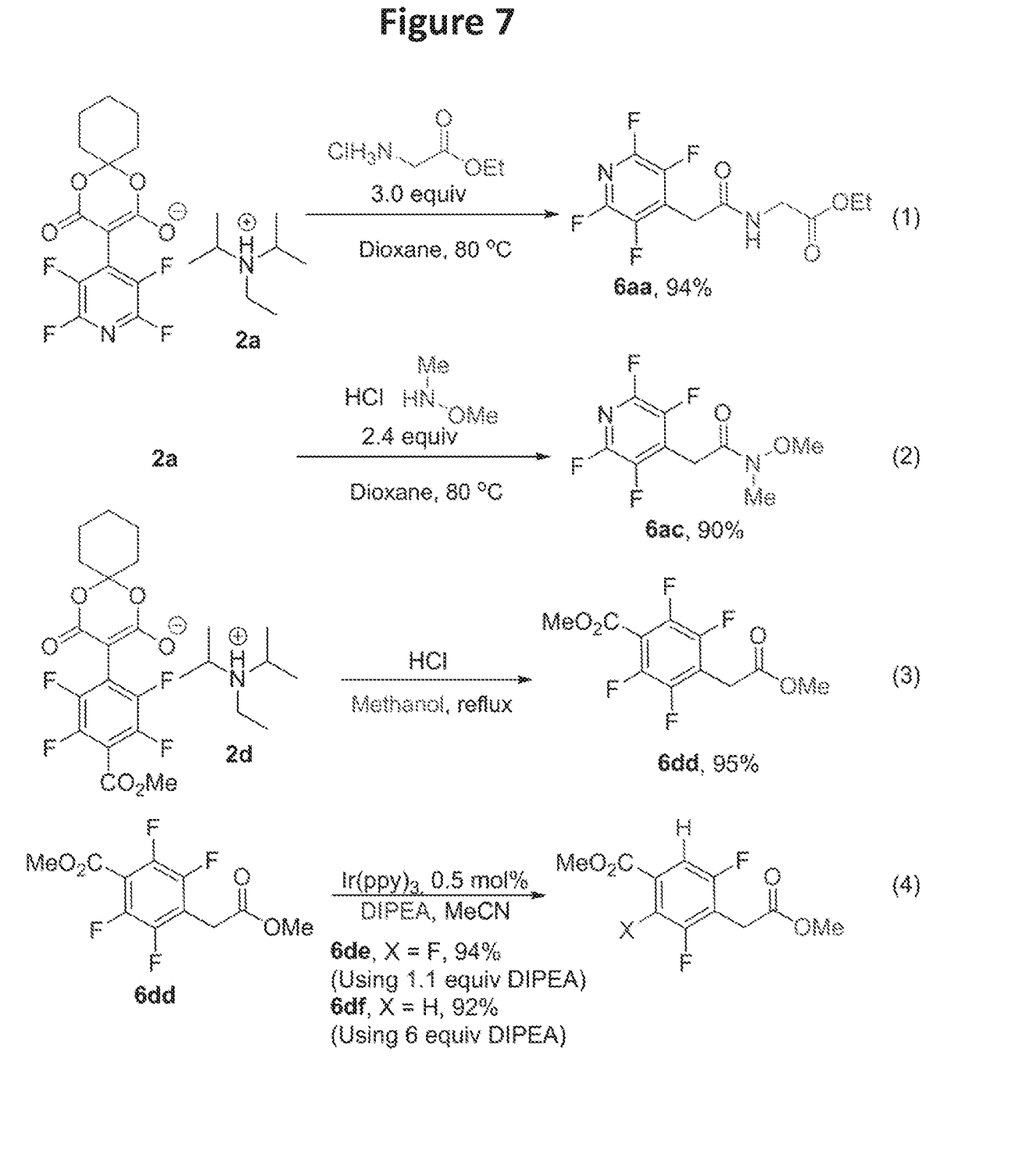
FIG. 7 illustrates some utility of the MA-adducts.
Figure 8:
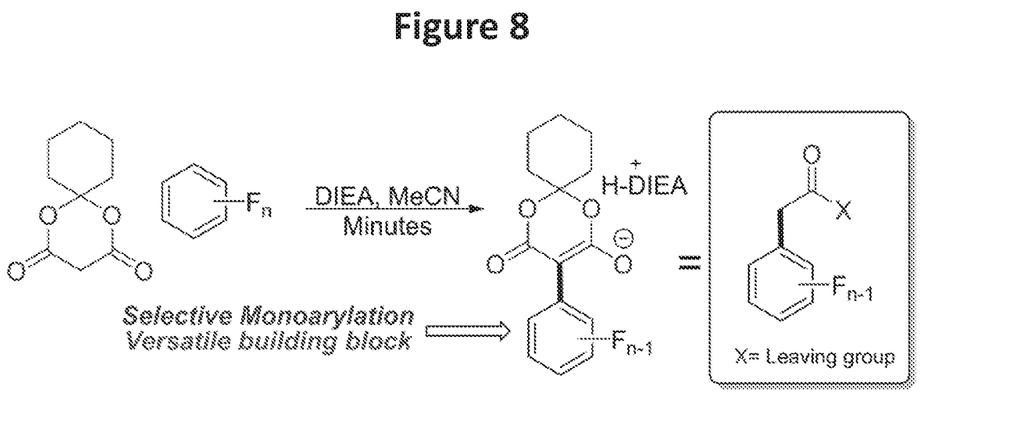
FIG. 8 illustrates an embodiment of the present disclosure.

Finally, the utility of the MA-adducts as highly functionalizable building blocks is demonstrated (e.g., FIG. 7). While the MA-adducts were stable under basic conditions, under acidic conditions, they undergo facile hydrolysis and nucleophilic addition. Under acidic conditions, nucleophilic attack of the carbonyl group and ring opening take place along with decarboxylation. The decarboxylation is significantly accelerated by presence of the perfluoroalkyl group such that it takes place readily at methanolic reflux (and even at room temperature) rather than temperatures well over 100° C., typical of the relevant diacids. Glycine ethyl ester underwent smooth acylation to afford the N-addition product (6aa, equation (1), FIG. 7). The Weinreb amide, which is a useful synthetic intermediate for the formation of ketones, was easily formed by the addition of its HCl salt with gentle heating (6ac, equation (2)). Methanolysis of MA-adduct 2d (equation (3)) cleanly formed the dimethyl ester, which was subjected to photocatalytic hydrodefluorination (HDF) conditions. By controlling the equivalents of reductant (the aliphatic amine) and the reaction time, selective formation of both the mono-HDF product (6dda) and di-HDF (6ddb) (FIG. 7) were accomplished which allow access to a di- and trifluorinated arene that would be challenging to access by existing methods.

Figure 9:
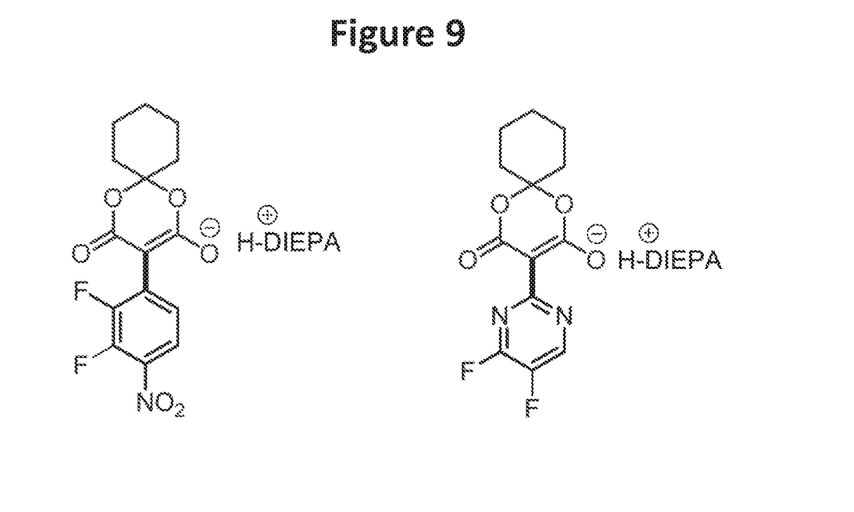
FIG. 9 contains an illustration of some substrates that work without perfluoroarylation according to the present disclosure.

FIG. 9 contains some additional compounds that were accessed according to the present disclosure.

In conclusion, the instant disclosure teaches conditions that facilitate the addition of Meldrum's acid to perfluoro- and polyfluoroarenes to arrive at synthetically versatile highly fluorinated building blocks. Furthermore, it has been shown that advantage can be taken of the relatively acidic nature of the products to prevent over arylation and to facilitate isolation. It is also shown that fully quaternerized carbons can be synthesized by reversing the order of events—which leverages the wealth of methods that exist for selective alkylation to circumvent the problematic alkylation. Given the increasing demand for fluorine incorporation into molecules of disparate fields, this simple method for construction of fluorinated building blocks will be of value for a broad spectrum of chemists.

Thus, the present disclosure is well adapted to carry out the objects and attain the ends and advantages mentioned above as well as those inherent therein. While the inventive concept(s) has been described and illustrated herein by reference to certain particular embodiments in relation to the drawings attached thereto, various changes and further modifications, apart from those shown or suggested herein, may be made therein by those of ordinary skill in the art, without departing from the spirit and scope of the inventive concept(s).

What is claimed is:

1. A composition, comprising:
a fluoroarylated Meldrum's acid or a salt thereof, wherein the fluoroarylated Meldrum's acid is represented by the Formula:

wherein:
at least one of $X_1$, $X_2$, $X_3$, and $X_4$ is a fluorine, and the three remaining of $X_1$, $X_2$, $X_3$, and $X_4$ are each independently selected from H and a halogen; and R and R' are together selected from (1) a single alkyl group and a H; (2) two alkyl groups; (3) a cyclic alkyl spiro group formed from the union of R and R'; or (4) an aryl spiro group formed from the union of R and R'.

2. The composition of claim 1, wherein the fluoroarylated Meldrum's acid has the structure:

3. The composition of claim 1, wherein the fluoroarylated Meldrum's acid has the structure:

4. The composition of claim 1, wherein the fluoroarylated Meldrum's acid has the structure:

5. The composition of claim 1, wherein R is a methyl group and R' is a methyl group.

6. The composition of claim 1, wherein R and R' together comprise a cyclohexyl spiro group.

7. A composition, comprising:
a fluoroarylated Meldrum's acid or a salt thereof, wherein the fluoroarylated Meldrum's acid is represented by the Formula:

wherein:
one of $X_1$, $X_2$, $X_3$, $X_4$, and $X_5$ is an activating functional group, at least one of the four remaining of $X_1$, $X_2$, $X_3$, $X_4$, and $X_5$ is a fluorine, and the remaining of $X_1$, $X_2$, $X_3$, $X_4$, and $X_5$ are each independently selected from H and a halogen; and
R and R' are together selected from (1) a single alkyl group and a H; (2) two alkyl groups; (3) a cyclic alkyl spiro group formed from the union of R and R'; or (4) an aryl spiro group formed from the union of R and R'.

8. The composition of claim 7, wherein R is a methyl group and R' is a methyl group.

9. The composition of claim 7, wherein R and R' together comprise a cyclohexyl spiro group.

10. The composition of claim 7, wherein the single activating functional group is selected from the group consisting of a pyridine, a pyrimidine, a nitro-substituted substrate, a ketone, a nitrile, an ester, a difluoromethyl group, a trifluoromethyl group, and a heterocycle substituted group.

11. The composition of claim 7, wherein the fluoroarylated Meldrum's acid has the structure:

12. The composition of claim 7, wherein the fluoroarylated Meldrum's acid has the structure:

13. The composition of claim 7, wherein the fluoroarylated Meldrum's acid has the structure:

14. The composition of claim 7, wherein the fluoroarylated Meldrum's acid has the structure:

15. The composition of claim 7, wherein the fluoroarylated Meldrum's acid has the structure:

16. The composition of claim 7, wherein the fluoroarylated Meldrum's acid has the structure:

17. The composition of claim 7, wherein the fluoroarylated Meldrum's acid has the structure:

18. The composition of claim 7, wherein the fluoroarylated Meldrum's acid has the structure:

19. A composition, comprising:
a fluoroarylated Meldrum's acid or a salt thereof, wherein the fluoroarylated Meldrum's acid is represented by the Formula:

wherein:
at least two of $X_1$, $X_2$, $X_3$, $X_4$, and $X_5$ are fluorines, and the three remaining of $X_1$, $X_2$, $X_3$, $X_4$, and $X_5$ are each independently selected from a halogen, H, and an activating functional group selected from the group consisting of a pyridine, a pyrimidine, a nitro-substituted substrate, a ketone, an ester, a difluoromethyl group, a trifluoromethyl group, and a heterocycle substituted group; and
R and R' are together selected from (1) a single alkyl group and a H; (2) two alkyl groups; (3) a cyclic alkyl spiro group formed from the union of R and R'; or (4) an aryl spiro group formed from the union of R and R'.

20. A composition, comprising:
a fluoroarylated Meldrum's acid or a salt thereof, wherein the fluoroarylated Meldrum's acid is represented by Formula I:

Formula I wherein:
$ArF_x$ is a fluorinated aromatic group, wherein x is in a range of from one fluorine up to n-1 fluorines, wherein n is defined as the number of fluorines present in a perfluorinated aromatic group ($ArF_n$) prior to attachment to the Meldrum's acid or salt thereof; and
R and R' are together selected from (1) a single alkyl group and a H; (2) two alkyl groups; (3) a cyclic alkyl spiro group formed from the union of R and R'; or (4) an aryl spiro group formed from the union of R and R'; and
with the proviso that the fluorinated aromatic group $ArF_x$ is only substituted with fluorine atoms and no non-fluorine atoms.

* * * * *

UNITED STATES PATENT AND TRADEMARK OFFICE
CERTIFICATE OF CORRECTION

PATENT NO. : 11,117,880 B2
APPLICATION NO. : 16/404110
DATED : September 14, 2021
INVENTOR(S) : Jimmie Dean Weaver and Sameera Senaweera It is certified that error appears in the above-identified patent and that said Letters Patent is hereby corrected as shown below:

In the Specification
Column 4, Line 43: Delete "6-diene)" and replace with -- 6-dione) --
Column 7, Line 1: Delete "perfluoroalkyl" and replace with -- perfluoroaryl --

In the Claims

Column 8, Lines 25-38 Claim 3: Delete the current structure and replace with -- 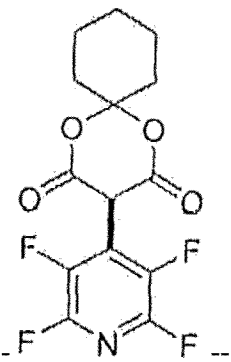 --

Signed and Sealed this
Sixteenth Day of November, 2021

Drew Hirshfeld
*Performing the Functions and Duties of the
Under Secretary of Commerce for Intellectual Property and
Director of the United States Patent and Trademark Office*